US009085792B2

(12) United States Patent
Colin et al.

(10) Patent No.: US 9,085,792 B2
(45) Date of Patent: Jul. 21, 2015

(54) METHODS FOR INOCULATING CULTURE MEDIA ON PETRI DISHES BY MEANS OF VIBRATION FREQUENCIES

(75) Inventors: Bruno Colin, Marcy l'Etoile (FR); Marie-Pierre Montet, Lyons (FR)

(73) Assignee: BIOMERIEUX, Marcy l'Etoile (FR)

( * ) Notice: Subject to any disclaimer, the term of this patent is extended or adjusted under 35 U.S.C. 154(b) by 0 days.

(21) Appl. No.: 14/238,673

(22) PCT Filed: Aug. 30, 2012

(86) PCT No.: PCT/FR2012/051956
§ 371 (c)(1),
(2), (4) Date: Feb. 12, 2014

(87) PCT Pub. No.: WO2013/030510
PCT Pub. Date: Mar. 7, 2013

(65) Prior Publication Data
US 2014/0220616 A1    Aug. 7, 2014

(30) Foreign Application Priority Data
Aug. 30, 2011   (FR) ...................................... 11 57619

(51) Int. Cl.
*C12Q 1/24*   (2006.01)
*C12M 1/22*   (2006.01)
*C12M 1/00*   (2006.01)
*C12M 1/26*   (2006.01)

(52) U.S. Cl.
CPC ................. *C12Q 1/24* (2013.01); *C12M 23/10* (2013.01); *C12M 23/38* (2013.01); *C12M 33/08* (2013.01)

(58) Field of Classification Search
IPC .................................. C12Q 1/24; C12M 23/10
See application file for complete search history.

(56) References Cited

U.S. PATENT DOCUMENTS 4,344,712 A    8/1982   Shaffer et al.

FOREIGN PATENT DOCUMENTS

| DE | 196 31 997 A1 | 2/1998 |
| DE | 10 2010 006 473 A1 | 8/2011 |
| GB | 1 278 531 | 6/1972 |
| JP | A-2008-131928 | 6/2008 |
| WO | WO 2006/087398 A1 | 8/2006 |

OTHER PUBLICATIONS

International Search Report issued in International Patent Application No. PCT/FR2012/051956 dated Oct. 29, 2012.
Written Opinion issued in International Patent Application No. PCT/FR2012/051956 dated Oct. 29, 2012 (with translation).
International Preliminary Report on Patentability issued in International Patent Application No. PCT/FR2012/051956 dated Mar. 4, 2014 (with translation).

*Primary Examiner* — Lora E Barnhart Driscoll
*Assistant Examiner* — Paul Martin
(74) *Attorney, Agent, or Firm* — Oliff PLC

(57) ABSTRACT

The present invention relates to a method for inoculating at least one agar culture medium, contained in a Petri dish, with at least one sample likely to contain microorganisms. The method includes the steps of: providing at least one agar culture medium contained in a Petri dish; providing the sample likely to contain microorganisms in liquid form; performing at least one deposition of the liquid sample onto the lid of the Petri dish such that the liquid sample can be transferred from the lid to the agar culture medium; and spraying the liquid sample, initially deposited onto the cover, onto the agar culture medium by vibrating the Petri dish.

11 Claims, 4 Drawing Sheets

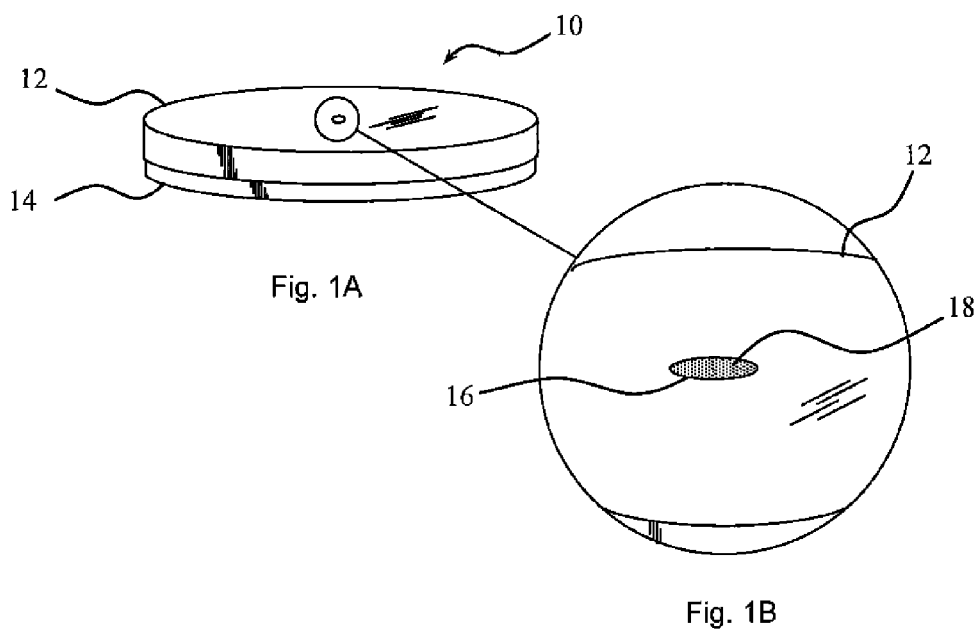
Fig. 1A
Fig. 1B
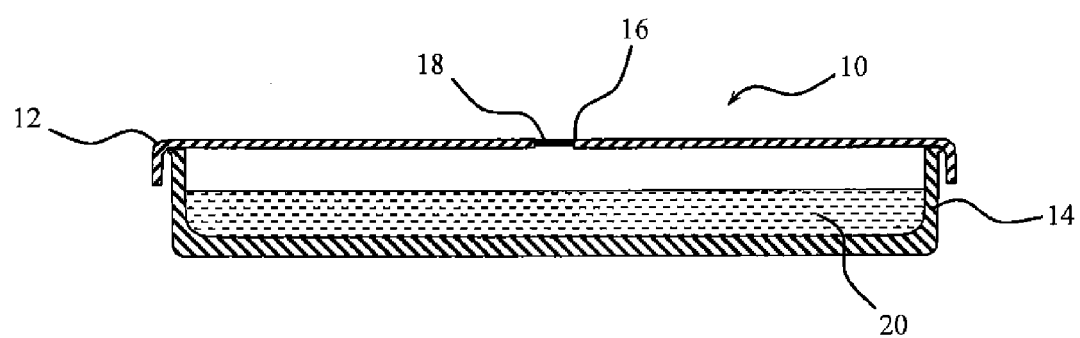
Fig. 2A

METHODS FOR INOCULATING CULTURE MEDIA ON PETRI DISHES BY MEANS OF VIBRATION FREQUENCIES

The technical field of the present invention is that of microbiology. More particularly, the present invention relates to a method for inoculating culture media contained in Petri dishes, with a sample, by means of vibration frequencies. The invention also relates to a Petri dish which makes it possible to implement said method.

In the fields of clinical diagnosis and of industrial food-processing, pharmaceutical or cosmetic microbiological testing, agar culture media in Petri dishes have for several decades constituted an essential tool for the detection and identification of microorganisms, optionally pathogenic microorganisms.

The inoculation of such culture media is conventionally carried out, manually, using an inoculation tool which is a disposable plastic loop, or a platinum loop which it is necessary to heat for the purpose of sterilization between two uses. The inoculation can also be carried out using a disposable pipette.

The inoculation can also be carried out automatically using systems developed and sold for this purpose. The function of such systems is in fact to automate the inoculation of culture media in Petri dishes, using automated mechanical parts. Such a system is for example sold by the applicant under the name Previ® Isola.

Whether by means of manual or automated techniques, the inoculation of culture media on Petri dishes requires prolonged opening of the latter in order to enable the inoculation process. The latter generally consists of streaking or counting, that is to say the inoculation tool which carries the sample that may contain microorganisms and which is brought into contact with the culture medium, is moved on the latter in order to deposit the sample, and therefore the microorganisms, on the culture medium. Thus, this prolonged opening can lead to risks of contamination of the culture medium by microorganisms other than those present in the sample, which come from the external environment. Moreover, the opposite effect is also liable to occur, that is to say the prolonged opening of the dish during the inoculation is capable of causing contamination of the external environment by the microorganism(s) present in the sample.

Document WO-A-2006/087398 describes a device for collecting a liquid sample which may contain microorganisms in a first top compartment and carrying out an inoculation of a culture medium in a Petri dish, in spray form, the Petri dish being placed in a second bottom compartment. The spraying is obtained by passing the sample through micronozzles, said micronozzles being opened by means of a pressure exerted by a pressure means.

While such a device can prove to be practical in certain specific cases, it has the major drawback of requiring several handling steps in order in particular to put in place the sample and the Petri dish. This is difficult to envision in the context of the sustained activity of a microbiology laboratory in which several tens of samples are handled per day.

Document DE 10 2010 006 473 describes a Petri dish, the lid of which has a through-hole closed by a septum. In this respect, the Petri dish described in said document makes it possible to inoculate the culture medium contained in said dish, without opening the lid, and thus to limit the risks of contamination.

The inoculation of the Petri dish is carried out using an accessory inoculation device which is positioned inside the dish and firmly attached to the lid of said dish. This device consists of a radial blade which ends with a lip that comes into contact with the culture medium during the inoculation, carried out by rotating the lid on the bottom of the dish.

The invention described in document DE 10 2010 006 473 has the main drawback of complicating the Petri dish, whereas the latter is basically a product of extreme simplicity, which is what makes it successful. Moreover, the use of an inoculation system as described does not make it possible to perform effective plating out operations for the purposes of streaking.

Document DE 196 31 997 describes a Petri dish, the lid of which has a spray nozzle and a pressure-equalizing system. Fluid to be introduced into the dish is sprayed using a pressurized device which connects onto the spray nozzle. The invention described in document DE 196 31 997 has the main drawback of being relatively complex compared with a standard Petri dish which is supposed to be extremely simple. This necessarily causes a considerable over-cost during the manufacturing of such a product.

From the viewpoint of the analysis of the existing circumstances, it therefore appears to be particularly advantageous to be able to have a method of inoculation which limits the risks of contamination while at the same time being simple to implement, which is readily adaptable in the context of a standard microbiology laboratory and which does not cause too great a modification to the Petri dish which is the basic tool of the microbiology laboratory.

The present invention proposes to solve the technical problems addressed above by providing a method for inoculating at least one agar culture medium, contained in a Petri dish, with at least one sample which may contain microorganisms, said method comprising the steps consisting in:
- a) providing at least one agar culture medium contained in a Petri dish;
- b) providing the sample which may contain microorganisms in liquid form;
- c) performing at least one deposition of the sample, in liquid form, onto the lid of the Petri dish such that said sample can be transferred from the lid to the agar culture medium;
- d) spraying the sample, initially deposited onto the lid, onto the agar culture medium, by vibrating the Petri dish.

According to one particular embodiment of the invention, the sample is deposited onto the internal face of the lid of the Petri dish.

Advantageously, the deposition of the sample onto the internal face of the lid, is performed through said lid. Said deposition of the liquid sample can in particular be carried out through a septum. Alternatively, the deposition of the liquid sample is carried out through a through-hole made in the lid. Said hole can be made by piercing, with the tool for depositing the liquid sample.

According to one alternative embodiment of the invention, the Petri dish is open in order to perform the sample deposition onto the internal face of the lid of said Petri dish.

According to another alternative embodiment of the invention, the deposition is carried out in at least one cavity, made in the lid. The cavity is open on the external face of the lid and has an orifice in the internal face of said lid.

Advantageously, during the spraying step, the vibration of the Petri dish is obtained by bringing the latter into contact with a vibration means. Even more advantageously, it is the lid of the Petri dish which is brought into contact with a vibration means.

Another subject of the invention relates to a Petri dish which comprises a lid and a base, in which the lid has at least one through-hole. According to one particular embodiment, the through-hole is closed up by a septum.

According to one alternative of the invention, the through-hole is located inside at least one cavity, made in the lid of said Petri dish and capable of receiving a liquid sample.

The objectives and advantages of the methods according to the present invention will be understood more clearly in the light of the in no way limiting example which follows, with reference to the drawing, in which:

FIG. 1A represents a perspective view of a Petri dish according to a first embodiment.

FIG. 1B represents a magnification of the Petri dish represented in FIG. 1A.

FIG. 2A represents a cross section of the Petri dish according to the first embodiment.

A first embodiment 10 of the Petri dish according to the invention is represented as a perspective on FIGS. 1A and 1B and as a cross section in FIG. 2A.

Figure 2B:
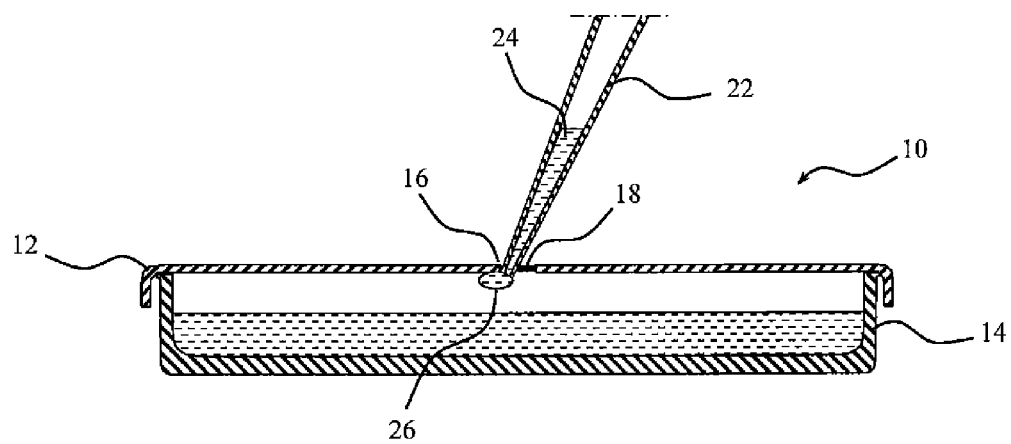
FIG. 2B represents a cross section of the Petri dish according to the first embodiment, during the step of depositing a drop of a sample to be analyzed.

This Petri dish 10 consists of a lid 12 and a bottom 14. These two components are conventionally made of a transparent polymer material, such as polystyrene. In a manner that is in no way limiting, the Petri dish 10 is in this case represented in its standard form, namely cylindrical with a round base. The lid 12 of the Petri dish 10 has, at its center, a through-hole 16. This through-hole 16 is in this case closed off with a membrane 18. This membrane must be made of a material which enables it to be pierced. In one preferential embodiment, this membrane 16 is an elastic membrane of septum type, which can be pierced using an appropriate tool and which has, moreover, the capacity to close up again. Such septa are well known and widely used in the medical field. As can be seen in FIG. 2A, the Petri dish moreover contains, within it, a layer of agar culture medium 20, which can be inoculated by means of an inoculating method according to the invention, which will be described hereinafter, in relation to FIGS. 2B to 2D.

Represented in FIG. 2B is the step of depositing a drop of liquid sample. More specifically, this step consists, firstly, in suctioning by means of a suction/discharge device 22 such as a pipette, a fraction of a sample 24 to be analyzed, in liquid form. Such a sample can actually be a liquid sample, such as:
body fluid, and in particular urine, blood, joint fluid;
liquid sample of food origin, such as a beverage;
environmental sample, such as a water specimen;
pharmaceutical or cosmetic sample.

The liquid sample 24 can also be an enrichment medium with which a primary sample has been mixed. Such a primary sample may be a liquid sample as described above, but also a solid sample, such as a food sample.

Finally, the liquid sample 24 may also be a suspension of microorganisms prepared from an isolate. Such an isolate may, for example, consist of bacterial colonies.

The suction/discharge device 22, filled with the fraction of sample 24 to be analyzed, is used to pierce the membrane 18 so as to allow the tip of said suction/discharge device 22 to pass through the lid 12, through the through-hole 16. The tip of the suction/discharge device 22 is then brought into contact with the internal face of the lid 12 so as to deposit a drop 26 of the sample 24 on said internal face.

Once the drop 26 has been deposited, the suction/discharge device 22 is removed. The elastic membrane 18 closes up again, thus limiting the risks of contamination inside the Petri dish 10. It can absolutely be envisioned to perform several deposits in the form of drops 26 onto the internal face of the lid 12.

Figure 2C:
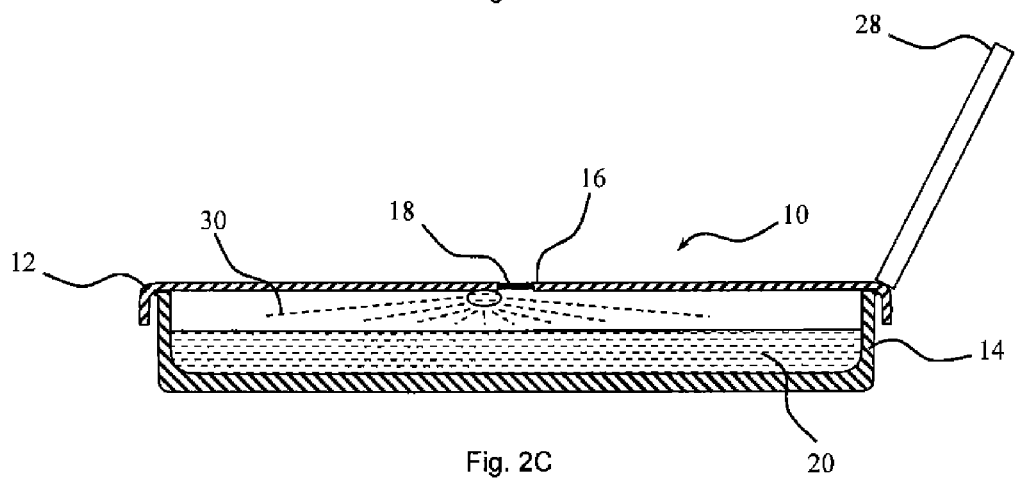
FIG. 2C represents a cross section of the Petri dish according to the first embodiment, during the step of spraying the liquid sample, by vibrating the Petri dish.

The next step, represented in FIG. 2C, consists in causing the lid 12 to vibrate in order to bring about spraying of the sample 24 from the drop 26 deposited onto the internal face of the lid 12. To this end, a vibration means 28, which is brought into contact with the lid 12, is used. Such a vibration means is, for example, a toothed wheel which is driven by a motor and which comes into contact with the Petri dish, preferentially with the lid of said Petri dish. Any other means for causing vibrations which is well known to those skilled in the art can also be used.

When the vibration means 28 is operated, it generates vibrations in the lid 12. The frequency of these vibrations is preferentially between 800 and 4500 hertz (Hz). These vibrations then generate spraying by projection of microdrops 30 of sample from the drop 26, in particular in the direction of the agar culture medium. This spraying generates a random dispersing, at the surface of the agar culture medium, of sample microdrops which may contain microorganisms such as bacteria. The result obtained is thus approximately equivalent to standard inoculation of a culture medium via the streaking technique.

Figure 2D:
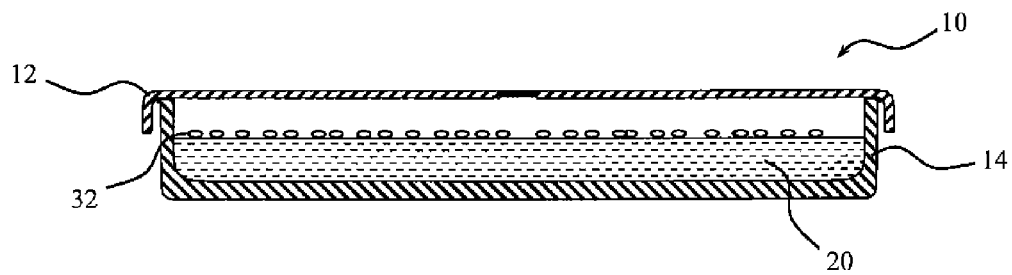
FIG. 2D represents a cross section of the Petri dish according to the first embodiment, once the liquid sample has been dispersed onto the culture medium in the form of droplets and the Petri dish has been incubated for a period of time required for the growth of the microorganisms.

After incubation of the Petri dish in an incubator for a period of between 12 and 72 h, the appearance of bacterial colonies 32 isolated from one another, as represented in FIG. 2D, is observed at the surface of the agar culture medium 20.

A second embodiment of the Petri dish according to the invention and of the related inoculating method are represented in FIGS. 3A to 3D.

Figure 3A:
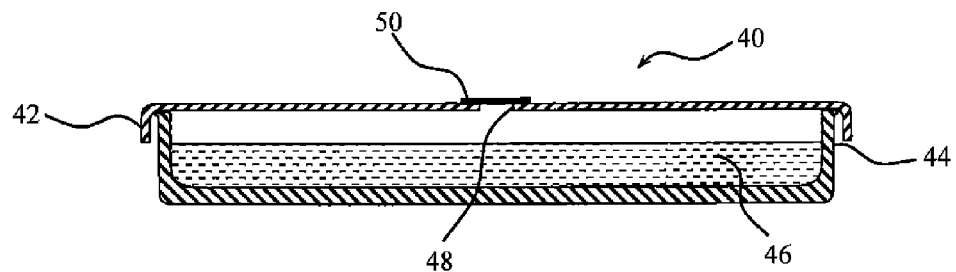
FIG. 3A represents a cross section of the Petri dish according to a second embodiment.

FIG. 3A shows a Petri dish 40, consisting of a lid 42 and a bottom 44. The lid 42 is positioned on the bottom 44. An agar culture medium 46 is contained inside this Petri dish.

The lid 42 of the Petri dish 40 has, at its center, a through-hole 48. This through-hole 48 is in this case closed up by a tab 50, thus avoiding any contamination between the inside of the Petri dish and the external environment. This tab 50 can consist of any material suitable for the function that it has. It can, for example, be based on paper or on polymer material. It may be monolayer or multilayer. It advantageously has, on the face in contact with the lid of the Petri dish, a layer of an adhesive material, the adhesive power of which must make it possible to detach said tab, but also to reattach it; optionally several times. It is, moreover, important for the dimensions of the tab 50 to be much larger than the dimensions of the through-hole 48, in order to limit as much as possible the exchanges between the outside and the inside of the Petri dish.

Figure 3B:
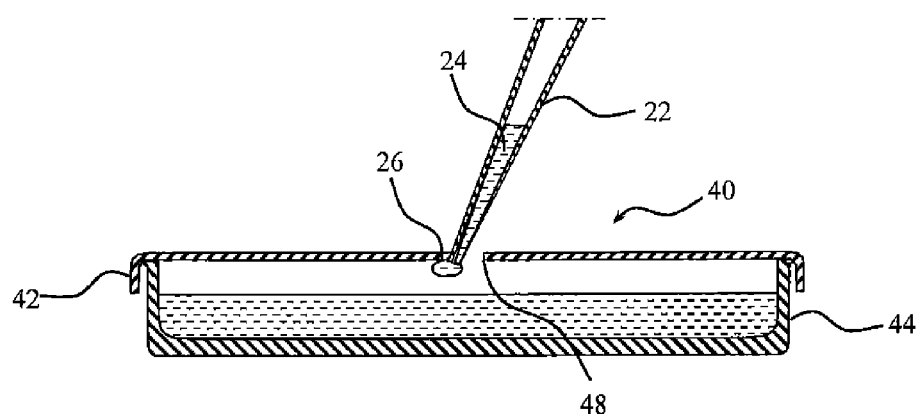
FIG. 3B represents a cross section of the Petri dish according to the second embodiment, during the step of depositing a drop of a sample to be analyzed.
Figure 3C:
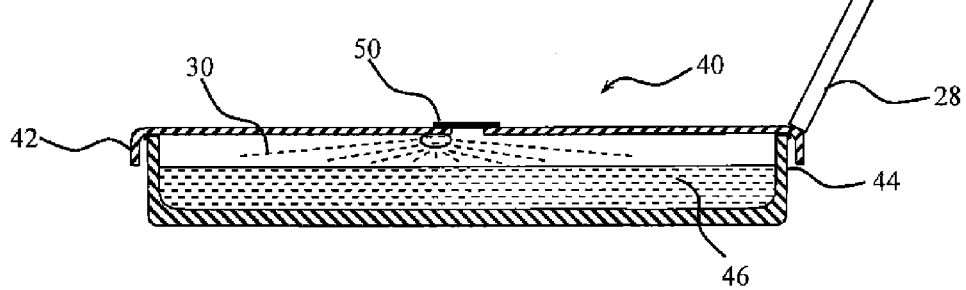
FIG. 3C represents a cross section of the Petri dish according to the second embodiment, during the step of spraying the liquid sample, by vibrating the Petri dish.

Represented in FIG. 3B is the step of depositing a drop of liquid sample. More specifically, this step consists firstly in suctioning, by means of a suction/discharge device 22, a fraction of a sample 24 to be analyzed, in liquid form.

In order to allow the deposition of one or more drops of the sample 24 on the internal face of the lid 42, the tab 50 (not represented in FIG. 3B) is detached. The detachment of the tab 50 may be partial or total. Indeed, it may be envisioned to partially detach the tab 50 so as to free the through-hole 48, or to completely remove said tab from the lid 42. It is this alternative which is represented in FIG. 3B. Each of these alternatives has advantages and disadvantages. Partial detachment has the advantage of allowing easier reattachment. It nevertheless has the disadvantage of increasing the risks of contamination of the tab 50 with the sample 24 by means of the tip of the suction/discharge device 22, during the introduction of the latter through the through-hole 48. Complete detachment of the tab 50 has the main advantage of preventing any risk of contamination of the latter. On the other hand, it requires placing the tab 50 in a safe place for the period of time required for depositing the sample 24 in the Petri dish 40, then repositioning said tab 50 optimally on the lid in order to ensure effective closing up of the through-hole 48.

Once the through-hole 48 has been made accessible, the suction/discharge device 22, filled with the fraction of sample 24 to be analyzed, is positioned so as to allow the tip of said suction/discharge device 22 to pass through the lid 12 through the through-hole 48. The tip of the suction/discharge device 22 is then brought into contact with the internal face of the lid 12 so as to deposit at least one drop 26 of the sample 24 onto said internal face.

Once the drop(s) 26 has (have) been deposited, the suction/discharge device 22 is withdrawn. The tab 50 is then repositioned, thus limiting the risks of contamination inside the Petri dish 40. This is presented in FIG. 3C. It is then possible to cause the lid 12 to vibrate in order to bring about the spraying of the sample 24 from the drop 26 deposited on the internal face of the lid 12. To this end, a vibration means 28, brought into contact with the lid 12, as already explained above, in relation to FIG. 2C, is used. These vibrations then generate spraying by projection of microdrops 30 of sample from the drop 26, in particular in the direction of the agar culture medium. This spraying generates a random dispersing, at the surface of the agar culture medium, of sample microdrops which may contain microorganisms such as bacteria. The result obtained is thus approximately identical to a standard inoculation of a culture medium via the streaking technique.

Figure 3D:
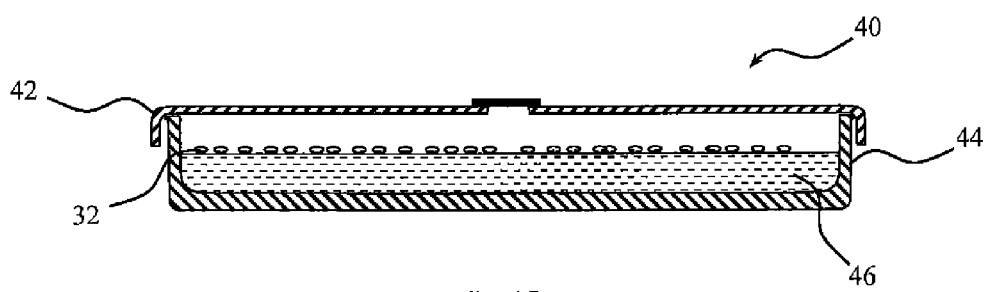
FIG. 3D represents a cross section of the Petri dish according to the second embodiment, once the liquid sample has been dispersed onto the culture medium in the form of droplets and the Petri dish has been incubated for a period of time required for the growth of the microorganisms.

After incubation of the Petri dish in an incubator for a period of time of between 12 and 72 h, the appearance of bacterial colonies 32 isolated from one another, as represented in FIG. 3D, is observed at the surface of the agar culture medium 46.

A third embodiment of the Petri dish according to the invention and of the related inoculation method are represented in relation to FIGS. 4A to 4D. The Petri dish 50, according to this third embodiment, consists of a lid 52 and a bottom 54. The lid 52 is positioned on the bottom 54. An agar culture medium 56 is contained inside this Petri dish.

The lid 52 of the Petri dish 50 has, at its center, a cavity 58 made in said lid 52 and which is intended to receive a deposit of liquid sample to be analyzed. This cavity 58 comprises a through-hole 60 in its bottom, such that it is in fluidic communication with the inside of the Petri dish 50. The cavity 58 is closed up in its upper part by a tab 62, thus avoiding, on the one hand, contamination of said cavity and, on the other hand, any communication between the inside of the Petri dish and the external environment. This tab 62 is identical or similar to the tab 50 described above and likewise the method for using it.

Figure 4A:
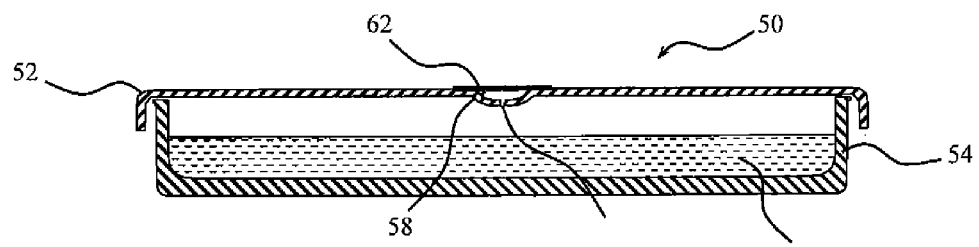
FIG. 4A represents a cross section of the Petri dish according to a third embodiment.
Figure 4B:
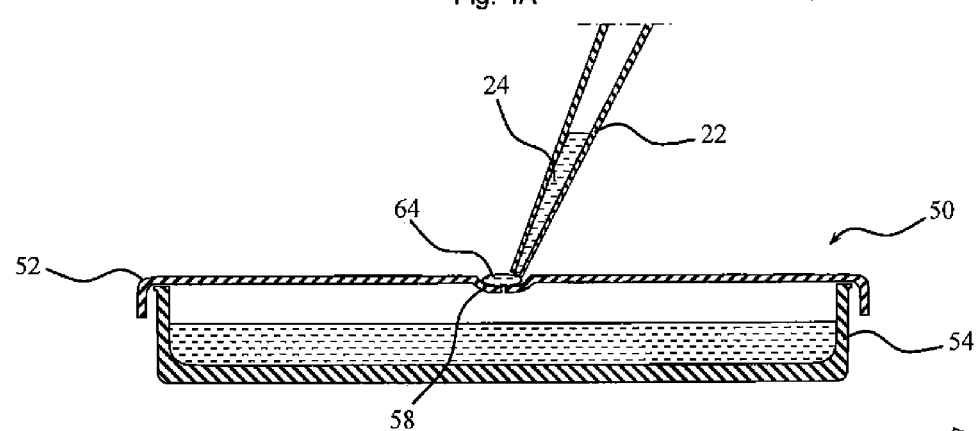
FIG. 4B represents a cross section of the Petri dish according to the third embodiment, during the step of depositing a drop of a sample to be analyzed.

Thus, represented in FIG. 4B is the step of depositing a drop of liquid sample inside the cavity. More specifically, this step consists firstly in suctioning, by means of a suction/discharge device 22, a fraction of a sample 24 to be analyzed, in liquid form.

In order to enable the deposition of one or more drops of the sample 24 inside the cavity 58, the tab 62 (not represented in FIG. 3B) is detached. The detachment of the tab 62 may be partial or total, as explained above. Once the cavity 58 has been made accessible, the suction/discharge device 22, filled with the fraction of sample 24 to be analyzed, is positioned in line with the cavity 58, so as to deposit at least one drop 64 of the sample 24 at the bottom of said cavity 58. It should be noted that the through-hole 60 made at the bottom of the cavity 58 must have a diameter that is sufficiently small for it to prevent the liquid consisting of the drop(s) 64 from pouring into the Petri dish passively. However, it should also have a diameter that is sufficiently large to allow the transfer of the liquid sample when it is performed, in particular by means of vibrations, as presented below.

Figure 4C:
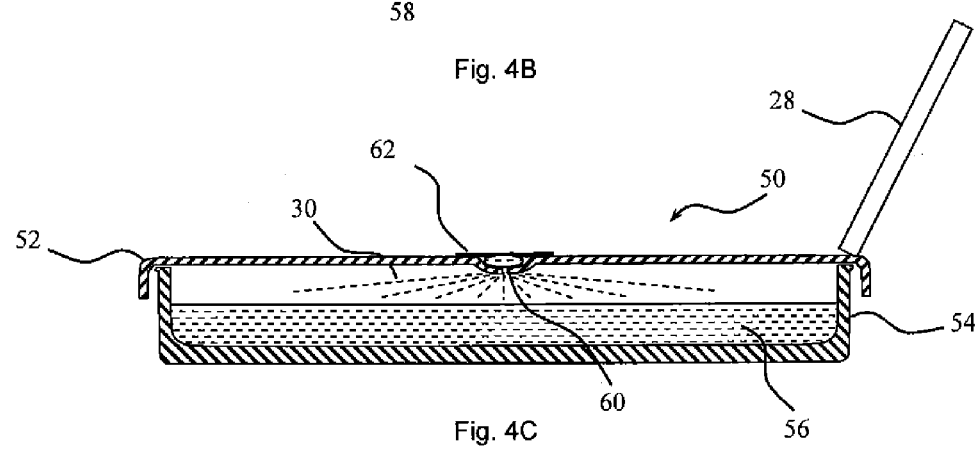
FIG. 4C represents a cross section of the Petri dish according to the third embodiment, during the step of spraying the liquid sample, by vibrating the Petri dish.

Once the drop(s) 64 have been deposited, the tab 62 is then repositioned on the cavity, thus eliminating risks of contamination. This is shown in FIG. 4C. It is then possible to cause the lid 52 to vibrate in order to bring about spraying of the sample 24 from the drop 64, deposited in the cavity 58, through the through-hole 60. To this end, a vibration means 28, brought into contact with the lid 12, as already explained above, in relation to FIGS. 2C and 3C, is used. These vibrations then generate spraying by projection of microdrops 30 of sample from the drop 64, in particular in the direction of the agar culture medium. This spraying generates a random dispersing, at the surface of the agar culture medium, of sample microdrops that may contain microorganisms such as bacteria. The result obtained is thus approximately identical to a standard inoculation of a culture medium via the streaking technique.

Figure 4D:
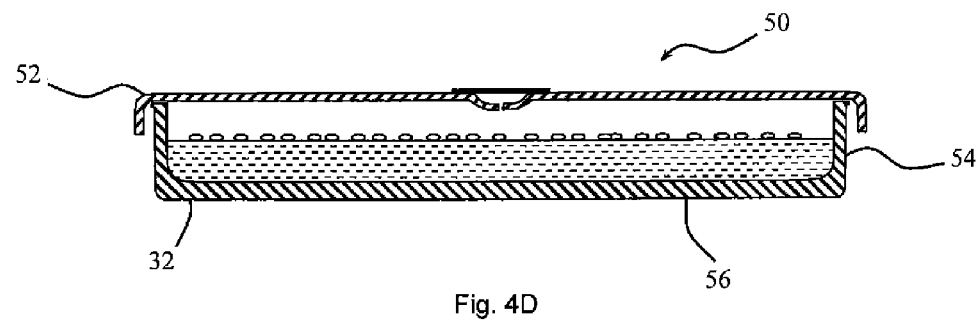
FIG. 4D represents a cross section of the Petri dish according to the third embodiment, once the liquid sample has been dispersed onto the culture medium in the form of droplets and the Petri dish has been incubated for a period of time required for the growth of the microorganisms.

After incubation of the Petri dish in an incubator for a period of time of between 12 and 72 h, the appearance of bacteria colonies 32 isolated from one another, as represented in FIG. 4D, is observed at the surface of the agar culture medium 56.

The invention claimed is:

1. A method for inoculating at least one agar culture medium, contained in a Petri dish, with at least one sample which may contain microorganisms, said method comprising the steps of:

a) providing at least one agar culture medium contained in a Petri dish;
b) providing the sample which may contain microorganisms in liquid form;
c) depositing the sample in liquid form onto the lid of the Petri dish such that said sample can be transferred from the lid to the agar culture medium; and
d) dispersing the sample, initially deposited onto the lid, onto the agar culture medium, by vibrating the Petri dish.

2. The method as claimed in claim 1, wherein the depositing of the sample is carried out onto the internal face of the lid of the Petri dish.

3. The method as claimed in claim 2, wherein the depositing of the sample onto the internal face of the lid, is carried out through said lid.

4. The method as claimed in claim 3, wherein the depositing of the sample is carried out through a self-closing septum in said lid.

5. The method as claimed in claim 3, wherein the depositing of the sample is carried out through a hole made in the lid.

6. The method as claimed in claim 5, wherein a tool for depositing the sample pierces said lid to create the hole.

7. The method as claimed in claim 2, wherein the Petri dish is open in order to perform the sample deposition onto the internal face of the lid of said Petri dish.

8. The method as claimed in claim 1, wherein the deposition is carried out in at least one cavity, made in the lid.

9. The method as claimed in claim 8, wherein the cavity is open on the external face of the lid and has an orifice in the internal face of said lid.

10. The method as claimed in claim 1, wherein during the dispersing step, the Petri dish is vibrated by bringing said dish into contact with a vibration means.

11. The method as claimed in claim 10, wherein, during the dispersing step, the lid of the Petri dish is brought into contact with said vibration means.

\* \* \* \* \*